United States Patent [19]

Fujiwara et al.

[11] 4,405,713
[45] Sep. 20, 1983

[54] PROCESS FOR THE PREPARATION OF OPTICALLY ACTIVE ANTHRACYCLINE GLYCOSIDES A AND B

[75] Inventors: Akiko Fujiwara; Tatsuo Hoshino, both of Kamakura, Japan

[73] Assignee: Hoffmann-La Roche Inc., Nutley, N.J.

[21] Appl. No.: 334,620

[22] Filed: Dec. 28, 1981

[51] Int. Cl.³ .................... C12P 19/56; C12R 1/465
[52] U.S. Cl. ...................................... 435/78; 435/886
[58] Field of Search ............ 435/74, 78, 84, 169, 435/886

[56] References Cited

U.S. PATENT DOCUMENTS 3,988,315  10/1976  Umezawa et al. .................. 435/78
4,329,339   5/1982  Fujiwara et al. .................... 435/78
4,375,511   3/1983  Fujiwara et al. .................. 435/886

OTHER PUBLICATIONS

Blumauerová et al., Genetics of Industrial Microorganisms, Proceedings of the Third Int. Sym. on Genetics of Ind. Microorg., Am. Soc. for Microbiol., Washington, D.C., 90–96 (1979).
Oki et al., J. Antibiotics, 33(11): 1331–1340 (1980).
Oki et al., J. Antibiotics, 28(10), 830–834 (1975).

Primary Examiner—Esther M. Kepplinger
Attorney, Agent, or Firm—Jon S. Saxe; Bernard S. Leon; Frank P. Hoffman

[57] ABSTRACT

There is presented the compounds 4-deoxy-aclacinomycin A and B and pharmaceutical preparations containing the same. The preparations are effective against bacteria and tumours. Also presented is a process for the preparation of optically active anthracycline glycosides A and B with the 7S-configuration starting from racemic anthracyclinones.

6 Claims, No Drawings

PROCESS FOR THE PREPARATION OF OPTICALLY ACTIVE ANTHRACYCLINE GLYCOSIDES A AND B

DESCRIPTION OF THE INVENTION

The present invention relates to novel 4-deoxy-aclacinomycin A and B, to pharmaceutical preparations containing the same which are effective against bacteria and tumours and to a process for the preparation of optically active anthracycline glycosides A and B with 7S-configuration starting from racemic anthracyclinones.

More particularly, the present invention is concerned with a process for the preparation of optically active anthracycline glycosides A and B having 7S-configuration by stereoselectively glycosidating an anthracyclinone with 7S-configuration starting from a racemic anthracyclinone with the aid of *Streptomyces galilaeus* OBB-111-848 (FERM-P No. 5316, ATCC 31598).

The sugar parts of the optically active anthracycline glycosides A and B of the present invention have the following formulae respectively:

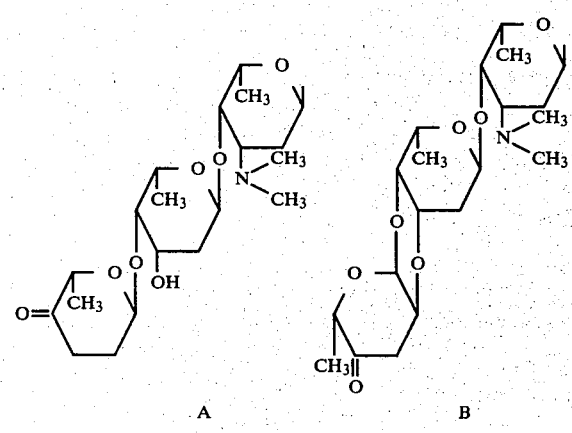

It has been known that natural type of anthracycline glycosides having 7S, 9R, 10R-configuration can be produced biosynthetically from natural type of anthracyclinones with 7S, 9R, 10R-configuration. For example, in the article, i.e. Oki et al., [Biosynthesis of anthracycline antibiotics by *Streptomyces galilaeus*", J. Antibiotics 33, 1331–1340, 1980, it is reported that natural type of anthracycline glycosides with 7S, 9R, 10R-configuration such as aclacinomycin A, 10-decarbomethoxyaclacinomycin A, 4-O-methylaclacinomycin A and cinerubin A can be prepared from natural type of anthracyclinones with 7S, 9R, 10R-configuration such as aklavinone, 10-decarbomethoxyalkavinone, 4-O-methylaklavinone and ε-pyrromycine, respectively with the aid of the mutant of *Streptomyces galilaeus* MA144-M1, i.e. the strain KE303. However, according to the said conventional glycosidation process, the starting materials, i.e. optically active anthracyclinones, are prepared by a fermentation method. In the said fermentation method, the optically active anthracyclinones can be obtained by using mutant strains derived from anthracycline glycosides-producing strains. In this case, a variety or amount of such natural type of anthracyclinones to be supplied is limited depending on the kind and yield of fermentation products. Furthermore, the manufacture of optically active anthracycline glycosides by a chemical synthesis requires many complicated steps such as the resolution, separation and the like.

According to the process of the present invention, racemic anthracyclinones are readily glycosidated stereoselectively by the above mentioned microorganism to yield optically active anthracycline glycosides. Thus, the present process provides an efficient practical method for the preparation of various optically active anthracycline glycosides in wide range, starting from different racemic anthracyclinones which may be synthesized by chemical method.

It is surprising that the glycosidation of racemic anthracyclinones is stereoselectively effected to attach sugars to only enantiomer with 7S-configuration to give optically active anthracycline glycosides A and B.

Typical examples of racemic anthracyclinones used as starting materials in the process of the present invention are aklavinone, 4-deoxy-aklavinone, ε-pyrromycine, 4-deoxy-ε-pyrromycinone, auramycinone, 4-deoxy-auramycinone, 4-fluoro-aklavinone and the like.

Although not part of the present invention the following reaction schemes provide methods to make novel intermediate aklavinones which can thereafter be glycosidated following the steps of the present invention.

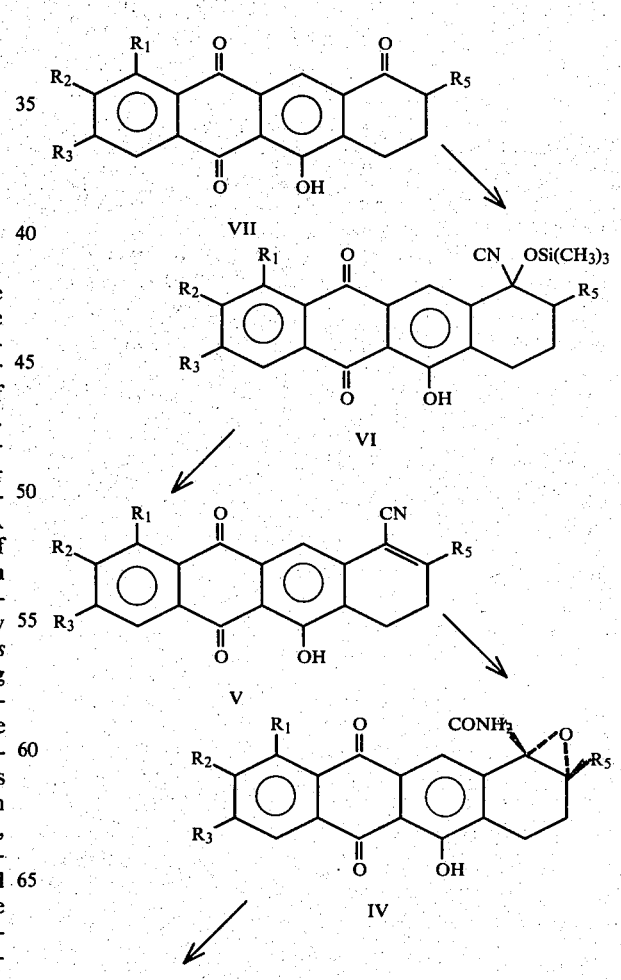

-continued

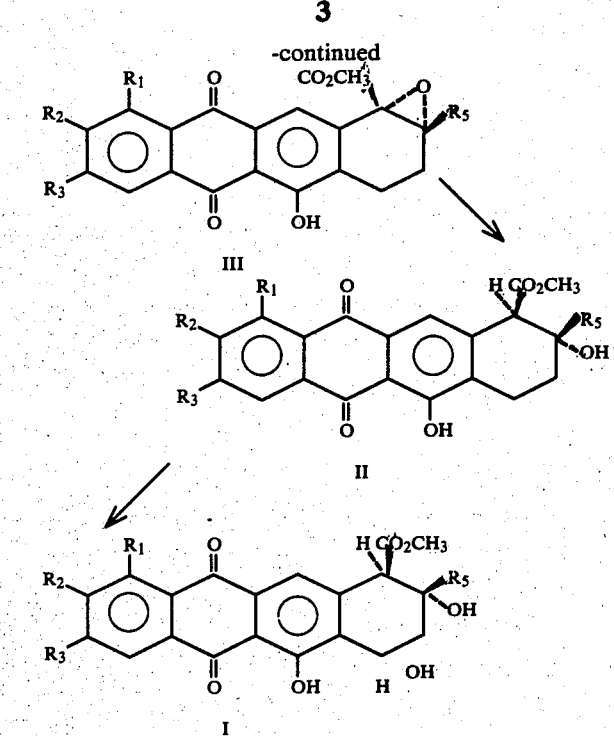

wherein $R_1$, $R_2$ and $R_3$ are selected from the group consisting of hydrogen, hydroxy, lower alkyl, lower alkoxy, and halo and $R_5$ is hydrogen, lower alkyl, and

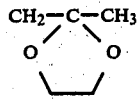

with the limitation that $R_1$, $R_2$ and $R_3$ are not all hydrogen.

The starting materials, compounds of formula VII, are well-known in the art and may be produced according to R. K. Boeckman, M. H. Delton, T. M. Dolak, T. Watanabe, and M. D. Glick, *J. Org. Chem.*, 44 (24), 4396-4402 (1980). In addition several compounds of formula II are known substances having been disclosed in articles by W. D. Ollis et al., *Proc. Chem. Soc. (London)*, 349 (1960);

Brockmann and Lenk, *Chem. Ber.*, 92, 1880 (1959); and

Brockmann and Lenk, *Naturwissenchaften*, 135 (1960), and by processes as set forth herein.

VII→VI

The starting material of formula VII is reacted with trimethylsilylcyanide in the presence of a Lewis acid catalyst. Solvents suitable for such a reaction are halocarbons, preferably methylene chloride, ethers, aromatic hydrocarbons, and other inert solvents. The temperature at which such a reaction may be affected ranges from 0° to 50° C. with room temperature preferred. Suitable Lewis acid catalysts are zinc halides, aluminum halides, and tin halides with zinc iodide preferred. The above reaction is preferably run at atmospheric pressure.

VI→V

The compound of formula VI may be reacted thereafter in the presence of a dehydrating agent in order to convert it to a compound of formula V. Suitable dehydrating agents include aryl and alkyl sulfonic acids in an inert aromatic solvent such as benzene, toluene, and xylene. Alternatively, potassium bisulfate may be used either in a suitable solvent or, preferably, without solvent. The reaction is affected at a temperature range of 70°-150° C. The reaction proceeds through an intermediate compound of formula VI-A, which need not be isolated in practice.

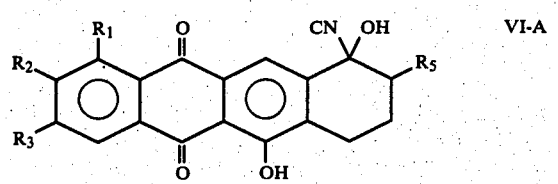

wherein $R_1$, $R_2$, $R_3$ and $R_5$ are as above.

V→IV

The compound of formula V is reacted with an alkaline aqueous solution of a peroxidizing agent for conversion to compounds of formula IV. Suitable peroxidizing agents include aryl and alkyl peracids, alkyl hydroperoxides, and hydrogen peroxide, the latter preferred. A co-solvent may be used, preferably a lower alkanol, preferably methanol, but is not absolutely necessary. The reaction may be affected over a temperature range of 0° to 50° C., room temperature is preferred.

IV→III

A compound of formula IV is treated with a methylating agent in an inert solvent and the resulting intermediate imidate ester of formula IV-A is hydrolyzed with aqueous acid.

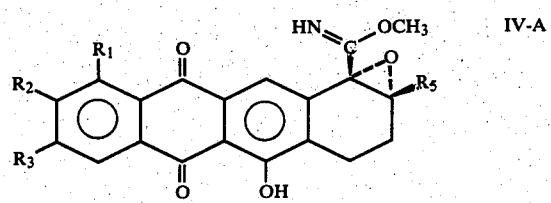

wherein $R_1$, $R_2$, $R_3$ and $R_5$ are as above.

Suitable methylating agents include dimethylsulfate, methyl iodide, and trimethyloxonium fluoroborate, the latter preferred. Inert solvents such as halocarbons, ethers, and the like, preferably methylene chloride are employed. The methylation can be conducted over a temperature range from −20° to 40° C. The hydrolysis of the intermediate IV-A from the methylation is carried out in dilute aqueous mineral acid, preferably 0.1 N sulfuric acid in the presence of an inert co-solvent, preferably tetrahydrofuran. This hydrolysis may be carried out over a temperature range from 25° to 80° (40° to 50° is preferred).

III→II

The compound of formula III is reacted with a reducing agent in order to convert it to a compound of formula II. Suitable reagents are zinc, aluminum amalgam, tin, and iron in a lower alkanoic acid, preferably zinc in acetic acid. Alternatively, catalytic hydrogen in the presence of a suitable catalyst such as nickel, palladium, platinum, and the like absorbed on typical supports such as carbon and barium sulfate. The hydrogenation is carried out in a lower alkanol, preferably ethanol, in the presence of an excess of an organic base such as triethylamine, piperidine, triethanolamine (preferred), and the like. The hydrogenation is carried out at one atmosphere of hydrogen and room temperature, preferably although higher pressures and temperatures are also suitable.

II→I

The compound of formula II may be reacted with a brominating agent, such as, N-bromosuccinimide or dibromantin in an inert nonpolar solvent, such as, carbon tetrachloride, chloroform, hexane or octane which may have the presence of small amounts of water at from about 60° C. to 100° C. preferably about 75° C. to 80° C. The presence of a free-radical initiator such as 2,2′-azobis-(2-methyl propionitrile) is preferable but not absolutely required. Thereafter the reaction mixture is treated with aqueous alkali metal (sodium or potassium) carbonate at about room temperature.

The microorganism used in the process provided by the present invention is *Streptomyces galilaeus* OBB-111-848 derived from the strain, *Streptomyces galilaeus* OBB-111 by treatment with N-methyl-N′-nitro-N-nitrosoguanidine. The present strain, *Streptomyces galilaeus* OBB-111 has been isolated from soils in Neuschwanstein, Oberbayern, West Germany. The strains, *Streptomyces galilaeus* OBB-111 and *Streptomyces galilaeus* OBB-111-848 have been deposited in the Agency of Industrial Science and Technology, Fermentation Research Institute, Japan, under FERM-P No. 4780 and FERM-P No. 5316, respectively and at the American Type Culture Collection, Rockville, Md., U.S.A. under ATCC Nos. 31533 and 31598, respectively.

The mycological characteristics of *Streptomyces galilaeus* OBB-111 are as follows:

1. Morphological properties:

The strain OBB-111 (FERM-P No. 4780, ATCC 31533) forms moderately long aerial mycelium from substrate mycelium. Hooks or spirals are observed to develop at the apex of the aerial mycelium, but no whorls are formed.

Mature spore chains with more than 10 spores per chain are usually produced. The spores are cylindrical, measure 0.5 to 0.6μ×0.8 to 1.0μ and their surface is smooth.

2. Culture characteristics on various media:

The culture characteristics of strain OBB-111 are shown in Table 1 hereinafter

The colour of the growth of strain OBB-111 on sucrose-nitrate agar, glycerol-asparagine agar, starch-inorganic salts agar and oatmeal agar changes to pink-violet with the dropwise addition of 0.05 N sodium hydroxide solution.

TABLE 1

| Culture characteristics of strain OBB-111 | |
|---|---|
| Medium | Strain OBB-111 |
| Sucrose-nitrate agar | |
| Growth | dull orange (4pe, Orange Rust) |
| Aerial Mycelium | brownish gray (3cb, Sand) |
| Diffusible Pigment | ~ pale orange (5cb) reddish |
| Glucose-asparagine agar | |
| Growth | dull orange (3pe, Topaz ~ 3ne, Topaz) |
| Aerial Mycelium | light brownish gray (3dc, Natural) |
| Diffusible Pigment | brownish |
| Glycerol-asparagine agar (ISP medium No. 5) | |
| Growth | pale yellow (3ge, Light Tan) ~ pale yellowish brown (31c, Amber) |
| Aerial Mycelium | light gray (2fe, Covert Gray) |
| Diffusible Pigment | none |
| Starch-inorganic salts agar (ISP medium No. 4) | |
| Growth | pale yellow (2pc, Bright Gold) ~ dull yellow (2pe, Mustard Gold) |
| Aerial Mycelium | light brownish gray (2dc, Natural) ~ light gray (2fe, Covert Gray) |
| Diffusible Pigment | yellow |
| Tyrosine agar (ISP medium No. 7) | |
| Growth | dark brownish gray (3ni, Clove Brown) |
| Aerial Mycelium | none |
| Diffusible Pigment | black |
| Nutrient agar | |
| Growth | colourless pale brown |
| Aerial Mycelium | none |
| Diffusible Pigment | none |
| Yeast extract-malt extract agar (ISP medium No. 2) | |
| Growth | yellowish brown (3ng, Yellow Maple) |
| Aerial Mycelium | light gray (2fe, Covert Gray) |
| Diffusible Pigment | none |
| Oatmeal agar (ISP medium No. 3) | |
| Growth | pale yellowish brown (2gc, Bamboo) ~ pale brown (3ie, Camel) |
| Aerial Mycelium | light gray (2fe, Covert Gray ~ 3fe, Silver Gray) |
| Diffusible Pigment | brown |
| Skimmed milk (37° C.) | |
| Growth | brown ~ dark brown |
| Aerial Mycelium | white ~ brownish gray |
| Diffusible Pigment | dark brown |
| Glucose peptone gelatin stab | |
| Growth | pale yellow |
| Aerial Mycelium | none |
| Diffusible Pigment | brown |

3. Physiological characteristics:

The physiological characteristics and carbohydrate utilisation of the strain OBB-111 are shown in the following Tables 2 and 3, respectively. The growth temperature was examined on yeast extract-malt extract agar (ISP medium No. 2) at 5°, 20°, 27°, 32°, 37°, 45° and 55° C. The optimal temperature for growth is 27° C. to 32° C. and no growth occurs at 5°, 45° and 55° C.

TABLE 2

Physiological characteristics of strain OBB-111

| Test | Response | Method and Materials Used |
|---|---|---|
| Gelatin liquefaction | moderate liquefaction | glucose-peptone-gelatin medium; 27° C. |
| Starch hydrolysis | weak to moderate hydrolysis | starch-inorganic salts agar |
| Peptonisation and coagulation of skimmed milk | moderate to strong peptonisation and no coagulation | 10% skimmed milk; 37° C. |
| Nitrate reduction | positive | ISP medium No. 8; 27° C. |
| Melanin formation | positive | ISP medium No. 1 ISP medium No. 6 ISP medium No. 7 |

TABLE 3

Carbohydrate utilization of strain OBB-111

| | |
|---|---|
| L-Arabinose | positive |
| D-Xylose | positive |
| Glucose | positive |
| D-Fructose | positive |
| Sucrose | positive |
| Inositol | positive |
| L-Rhamnose | positive |
| Raffinose | positive |
| D-Mannitol | negative |

Basal medium: Pridham-Gottlieb medium (ISP medium No. 9)
Temperature: 27° C.

The foregoing characteristics of strain OBB-111 can be summarised as follows: The strain belongs to the genus Streptomyces. The aerial mycelium forms spirals at the apex but no whorls. The surface of the spores is smooth. The growth on various media is found to be pale yellowish brown to pale brown or dull orange, and the aerial mycelium is light gray. The strain produces reddish to brown diffusible pigment and melanin on various media. Among known species of Streptomyces, strain OBB-111 resembles Streptomyces galilaeus (Reference 1: Archiv für Mikrobiologie, 31, 356, 1958. Reference 2: The Actinomycetes, 2, 215, 1961. Reference 3: International Journal of Systematic Bacteriology, 22, 298, 1972) and Streptomyces galilaeus MA144-M1, FERM-P No. 2455 (Reference 1: J. Antibiotics 33, 1331-1340, 1980). The differences between the present strain and the standard strains of *S. galilaeus* ISP 5481 and *S. galilaeus* MA144-M1 (FERM-P No. 2455) were investigated by parallel cultures. The results are shown in Table 4 hereinafter.

TABLE 4

| | OBB-111 | S. galilaeus ISP 5481 | S. galilaeus MA 144-M1 (FERM-P No. 2455) |
|---|---|---|---|
| Liquefaction of gelatin | moderate | weak to moderate | weak to moderate |
| Coagulation of milk | negative | weak positive | negative |
| Diffusible Pigment | dark brown | light brown | dark brown |
| Change of colour of growth by 0.05 N sodium hydroxide solution: | | | |
| ISP medium No. 3 | pink to violet | — | pink to violet |
| ISP medium No. 4 | slight pink ~ violet | — | slight pink ~ violet |
| ISP medium No. 5 | violet | slight | violet |
| | violet | | |

From the results, the strain, OBB-111 is similar to *S. galilaeus* ISP 5481 and *S. galilaeus* MA144-M1 (FERM-P No. 2455) in morphology and colour of the growth and mycelium on various media, chromogenicity and utilization of carbohydrates. However, the strain, OBB-111 differs from *S. galilaeus* MA144-M1 (FERM-P No. 2455) in the liquefaction of gelatin and from S. galilaeus ISP 5481 in the coagulation of skimmed milk, the production of diffusible pigment and the change in the colour of growth by 0.05 N sodium hydroxide solution. Furthermore, the strain, OBB-111 can be distinguished from *S. galilaeus* MA144-M1 used as the parent strain in the aforementioned prior art, i.e. J. Antibiotics 33, 1331-1340, 1980, since the former cannot produce cinerubins, but the latter produces them.

*Streptomyces galilaeus* OBB-111-848 (FERM-P No. 5316; ATCC 31598) used in the present invention is the strain derived from *Streptomyces galilaeus* OBB-111 (FERM-P No. 4780, ATCC 31533) by the following method.

The spores of an agar slant culture of *Streptomyces galilaeus* OBB-111 (FERM-P No. 4780, ATCC 31533) were suspended in 10 ml of sterile physiological saline solution and filtered through a glass filter No. 3. The spores were resuspended and diluted 2-fold with 0.2 M tris buffer (pH 9.0) containing 2 mg/ml of N-methyl-N'-nitro-N-nitrosoguanidine and incubated at 27° C. for 60 minutes. Then the spores were collected on the Nucleopore filter (0.2 μm pore size), washed with 30 ml of sterile physiological saline solution and resuspended in 10 ml of sterile physiological saline solution. The spore suspension thus obtained was spread on the ISP-No. 2 medium in a Petri dish and incubated at 27° C. for 4-6 days. The colonies were picked up and transferred to an agar slant and incubated for 10-14 days.

The strain OBB-111-848 was selected as a mutant which lacked anthracycline pigment formation, but was able to form anthracycline glycosides when anthracyclinone was added.

The difference between the strain OBB-111 and the strain OBB-111-848 thus obtained was found in colour change by addition of 0.05 N NaOH solution to agar culture, i.e. no colour change was observed with the strain OBB-111-848. Furthermore, the strain OBB-111-848 formed more aerial mycelium on agar media compared to the parent strain. However, it did not form aerial mycelium on various nutrient agar tested. This fact differentiated the strain OBB-111-848 from the strain KE-303 (FERM-P No. 4808) forming aerial mycelium on nutrient agar, which was used in a glycosidation process described in the aforementioned prior art, i.e. J. Antibiotics 33, 1331-1340, 1980. Other cultural and physiological characteristics of the strain OBB-111-848 and its parent strain OBB-111 resemble each other.

According to the process provided by the present invention, the microorganism can be used in a form of the culture broth or mycelia isolated from the culture broth of the microorganism. The culture broth can be prepared by inoculating a suitable medium with the microorganism. The culture medium can contain carbon sources, nitrogen sources, inorganic salts and other nutrient substances suitable for the growth of the microorganism. The carbon sources, for example, are glucose, sucrose, dextrin, mannose, starch, lactose, glycerol and the like. The nitrogen sources, for example, are nitrogen-containing organic substances such as peptone, meat extract, yeast extract, corn steep liquor, casein and the like, or nitrogen-containing inorganic compounds such as nitrates and inorganic ammonium salts. Examples of inorganic salts are phosphates or sodium, potassium, manganese, maganesium, iron copper salts and the like.

The cultivation of the microorganism may be carried out as a submerged culture, as a shaking culture or as a stationary culture. In a preferred embodiment, the microorganism is cultured under aerobic conditions.

The process provided by the present invention may be conveniently carried out by adding a racemic anthracyclinone as a substrate to the cultivated microorganism in the culture medium. The concentration of the substrate is not particularly significant, but a concentration of 50 to 800 mg/l is preferred. The most preferable concentration is 100 to 400 mg/l. The stereoselective glycosidation in accordance with the invention process can be carried out by continuation of the incubation of the microorganism under the above mentioned conditions in the presence of the substrate to be stereoselectively glycosidated. The incubation time can vary depending on the composition of the culture medium, on the substrate used and on the concentration of substrate and microorganism. In general, an incubation time of 5-75 hours suffices. The incubation temperature generally lies between 20° C. and 35° C. Furthermore, the incubation is conveniently carried out at a pH of 4 to 8.

The substrate can be added to the culture of the microorganism during the cultivation or to the culture medium prior to sterilization or inoculation. However, the addition of the substrate may take place preferably after the microorganism has been cultivated for about 2 days. It is preferred that the substrate is added to the culture medium in a form of a solution thereof in an organic solvent such as dimethyl sulfoxide, methanol and the like, or an aqueous emulsion.

There are thus obtained optically active anthracycline glycosides A and B, however the enantiomer with 7R-configuration in the substrates used remains in the fermentation broth without any glycosidation thereof.

The optically active anthracycline glycosides A and B can be isolated from the fermentation mixture in a manner known per se; for example, by solvent extraction with an organic solvent such as chloroform, methanol, and the like and by chromatography on a carrier such as silica gel, aluminium oxide and the like.

According to another aspect of preferred embodiment of the process provided by the present invention, the stereoselective glycosidation may be also carried out in the presence of the mycelium isolated from the culture broth of the microorganism in a solution, for example, a buffer solution, in physiological salt solution, in fresh nutrient solution, in water and the like. The conditions of said reaction are the same as mentioned before.

As mentioned above, according to the process provided by the present invention, the microorganism can be used not only in a form of the growing state, but also in a form of the resting state in which the reaction is simplified.

The process provided by the present invention conveniently applies to the process for producing optically active anthracycline glycosides A and B, especially aclacinomycin A and B, 4-deoxy-aclacinomycin A and B, cinerubin A and B, 4-deoxycinerubin A and B, auramycin A and B, 4-deoxy-auramycin A and B, 4-fluoro-aclacinomycin A and B, and the like which are effective against bacteria and tumours, from racemic anthracyclinones, especially, aklavinone, 4-deoxy-aklavinone, ε-pyrromycine, 4-deoxy-ε-pyrromycine, auramycinone, 4-deoxy-auramycinone and 4-fluoro-aklavinone, respectively.

Aclacinomycin A and B, cinerubin A and B (See: J. Antibiotics, 30, S-70, 1977), and auramycin A and B (See: Japanese Kokai No. 157597/1980) are known compounds. However, 4-deoxy-aclacinomycin A and B, 4-deoxy-cinerubin A and B, 4-deoxy-auramycin A and B, and 4-fluoro-aclacinomycin A and B are novel compounds.

The present invention is also concerned with 4-deoxy-aclacinomycin A and B, and an antibacterial or antitumour agent which contains, as the active ingredient, 4-deoxy-aclacinomycin A and B.

The biological activities of 4-deoxy-aclacinomycin A and B are as follows.

Table 5 hereinafter shows the in vitro minimum inhibitory concentrations (MIC) of 4-deoxy-aclacinomycin A and B in respect of various microorganisms determined using the agar streak method.

TABLE 5

| Microorganisms | MIC ($\mu$g/ml) | |
|---|---|---|
| | 4-Deoxy-aclacinomycin A | 4-Deoxy-aclacinomycin B |
| Bacillus subtilis IAM 1027 | 0.39 | 6.25 |
| Sarcina lutea IAM 1009 | 0.19 | 0.39 |
| Staphylococcus aureus 209P IAM 1011 | 0.78 | 3.13 |
| Staphylococcus epidermidis IFO 12993 | 0.78 | 3.13 |
| Micrococcus flavus ATCC 10240 | 0.19 | 0.39 |
| Escherichia coli K-12 IAM 1264 | >100 | >100 |
| Pseudomonas aeruginosa IFO 12689 | >100 | >100 |
| Proteus vulgaris IAM 1025 | >100 | >100 |
| Klebsiella pheumonia IFO 3512 | >100 | >100 |

Antitumour activity of 4-deoxy-aclacinomycin A

4-Deoxy-aclacinomycin A obtained in the present invention was tested against P388 leukemia in mice. When male $CDF_1$ mice (5 week old) were inoculated with $10^6$ of P388 leukemia cells intraperitoneally and the antibiotic was administered through the same route on days 1, 5 and 9, the survival time of the treated mice was prolonged as shown in Table 6.

TABLE 6

| Total dose (mg/Kg) | Mean survival days | Increase in life span (%) |
|---|---|---|
| 5.6 | 11.5 ± 0.5 | 8 |
| 11.3 | 12.5 ± 0.5 | 18 |
| 22.5 | 13.0 ± 0.0 | 23 |
| 45 | 13.5 ± 0.5 | 27 |
| 90 | 16.5 ± 0.5 | 57 |

TABLE 6-continued

| Total dose (mg/Kg) | Mean survival days | Increase in life span (%) |
|---|---|---|
| Control | 10.6 ± 0.6 | 0 |

All the mice treated with 100 mg/kg of 4-deoxy-aclacinomycin A, i.p., survived more than 7 days.

As mentioned above, the toxicity of 4-deoxy-aclacinomycin A is very low as compared with that of aclacinomycin A.

The following Examples illustrate the present invention. Unless otherwise stated, the expression "natural" denotes 7S, 9R, 10R-configuration.

EXAMPLE 1

100 ml of sterilized medium in a 500 ml Erlenmeyer flask were inoculated with a slant culture of *Streptomyces galilaeus* OBB-111-848 (FERM-P. No. 5316, ATCC 31598). The composition of said medium is as follows: glucose 2%, soluble starch 2%, Pharma Media (Traders Oil Mill Co. U.S.A.) 1%, Nacl 0.3%, and $CaCO_3$ 0.3%. The flask was incubated at 27° C. for 3 days on a rotary shaker operating at 180 rpm.

5 ml of the culture thus obtained were seeded into a 500 ml Erlenmeyer flask containing 100 ml of medium with the same composition as mentioned above. After the cultivation at 27° C. for 2 days, 10 mg of racemic aklavinone dissolved in 1 ml of methanol were added to the flask and further incubated. The cultivation was carried out for 18 hours.

To the culture broth were added 200 ml of chloroform/methanol (1:1, v/v). The extract was concentrated and analyzed by high performance liquid chromatography (μ Bondapak C18; $H_{12}O$/MeOH-37:63 v/v containing PIC reagent B-7, Waters). There were formed 1.9 mg of aclacinomycin A and 0.64 mg of aclacinomycin B, each of which has the natural configuration.

EXAMPLE 2

In a manner analogous to that described in Example 1, using 10 mg of racemic 4-deoxy-aklavinone instead of racemic aklavinone, there were formed 2.2 mg of 4-deoxy-aclacinomycin A and 1.2 mg of 4-deoxy-aclacinomycin B, of the natural type respectively.

EXAMPLE 3

In a manner analogous to that described in Example 1, using 10 mg of racemic ε-pyrromycinone instead of racemic aklavinone, there were formed 2.7 mg of cinerubin A and 1.5 mg of cinerubin B, of the natural type respectively.

EXAMPLE 4

In a manner analogous to that described in Example 1, using 10 mg of racemic 4-deoxy-ε-pyrromycinone instead of racemic aklavinone, there were formed 2.3 mg of 4-deoxy-cinerubin A and 1.3 mg of 4-deoxy-cinerubin B, of the natural type respectively.

EXAMPLE 5

In a manner analogous to that described in Example 1, using 10 mg of racemic auramycinone instead of racemic aklavinone, there were formed 2 mg of auramycin A and 0.8 mg of auramycin B, of the natural type respectively.

EXAMPLE 6

In a manner analogous to that described in Example 1, using 10 mg of racemic 4-deoxy-auramycinone instead of racemic aklavinone, there were formed 2.7 mg of 4-deoxy-auramycin A and 1.0 mg of 4-deoxy-auramycin B, of the natural type respectively.

EXAMPLE 7

In a manner analogous to that described in Example 1, using 10 mg of racemic 4-fluoro-aklavinone instead of racemic aklavinone, there were formed 3 mg of 4-fluoro-aclacinomycin A and 1.5 mg of 4-fluoro-aclacinomycin B, of the natural type respectively.

EXAMPLE 8

100 ml of the culture obtained by the same method described in Example 1 were centrifuged. The cells thus obtained were suspended into 100 ml of sterilized saline solution in a 500 ml flask.

10 mg of racemic aklavinone in 1 ml of methanol were added to the suspension and incubated on a rotary shaker at 27° C. for 20 hours. To the reaction mixture were added 200 ml of chloroform/methanol (1:1, v/v). The extract was concentrated and analyzed by high performance liquid chromatography. There were formed 1.3 mg of aclacinomycin A and 1.2 mg of aclacinomycin B, of the natural type respectively.

EXAMPLE 9

In a manner analogous to that described in Example 8, using 10 mg of racemic 4-deoxy-aklavinone, there were formed 2.3 mg of 4-deoxy-aclacinomycin A and 1.7 mg of 4-deoxy-aclacinomycin B, of the natural type respectively.

EXAMPLE 10

In a manner analogous to that described in Example 8, using racemic ε-pyrromycinone, there were formed 1.8 mg of cinerubin A and 1.0 mg of cinerubin B, of the natural type respectively.

EXAMPLE 11

In a manner analogous to that described in Example 8, using 10 mg of racemic 4-deoxy-ε-pyrromycinone, there were formed 1.3 mg of 4-deoxy-cinerubin A and 1.2 mg of 4-deoxy-cinerubin B, of the natural type respectively.

EXAMPLE 12

In a manner analogous to that described in Example 8, using 10 mg of racemic auramycinone, there were formed 1.8 mg of auramycin A and 1.2 mg of auramycin B, of the natural type respectively.

EXAMPLE 13

In a manner analogous to that described in Example 8, using racemic 4-deoxy-auramycinone, there were formed 1.8 mg of 4-deoxy-auramycin A and 1.0 mg of 4-deoxy-auramycin B, of the natural type respectively.

EXAMPLE 14

In a manner analogous to that described in Example 8, using racemic 4-fluoro-aklavinone, there were formed 2.5 mg of 4-fluoro-aclacinomycin A and 2.1 mg of 4-fluoro-aclacinomycin B, of the natural type respectively.

EXAMPLE 15

The slant culture of *Streptomyces galilaeus* OBB-111-848 (FERM-P No. 5316, ATCC 31598) was inoculated into 100 ml of medium containing glucose 2%, soluble starch 2%, Pharma Media (Traders Oil Mill Co., U.S.A.) 1%, Nacl 0.3%, and $CaCO_3$ in a 500 ml Erlenmeyer flask and cultivated at 27° C. for 3 days on a rotary shaker operating at 180 rpm. 5 ml of the culture thus obtained were transferred into each of ten 500 ml Erlenmeyer flasks containing 100 ml of medium with the same composition as mentioned above and incubated for further 2 days under the same condition.

To each flask, 10 mg of racemic aklavinone dissolved in 1 ml of methanol were added and incubated at 27° C. for 20 hours on a rotary shaker.

The culture broth was centrifuged at 8,000 rpm for 10 minutes to separate the cells from the supernatant. The cells were extracted with 1 l of the solvent mixture of chloroform and methanol (1:1, v/v), to which 500 ml of water were added to separate chloroform layer. The supernatant, on the other hand, was extracted with the equal volume of chloroform. The extracts were combined and evaporated to dryness and dissolved in a small amount of toluene, to which was added silica gel. The suspension was shaken overnight at room temperature.

The silica gel was collected by filtration and extracted with chloroform/methanol (5:1, v/v). The extract was evaporated to dryness under reduced pressure and dissolved in a small amount of chloroform. The purification was performed by thin layer chromatography on silica gel 60, $F_{254}$ (Merck Co.), with the solvent system of toluene/methanol (10:1), whereby they were obtained 6 mg of aclacinomycin A (m.p. 150° C., $[\alpha]_D = -12.5°$, c=0.1 in $CHCl_3$) and 5.7 mg of aclacinomycin B (m.p. 165° C., $[\alpha]_D = +1°$, c=0.1 in $CHCl_3$), of the natural type respectively, as well as 35 mg of (7R, 9S, 10S)-aklavinone ($[\alpha]_D = -262°$, c=0.1 in $CHCl_3$).

EXAMPLE 16

In a manner analogous to that described in Example 15, using 100 mg of racemic 4-deoxy-aklavinone, there were obtained 13.1 mg of 4-deoxy-aclacinomycin A (m.p. 141° C. $[\alpha]_D = -57.5°$ c=0.1 in $CHCl_3$) and 5.1 mg of 4-deoxy-aclacinomycin B (m.p. 115° C., $[\alpha]_D = -32.5°$, c=0.1 in $CHCl_3$) of the natural type respectively, as well as (7R, 9S, 10S)-4-deoxy-aklavinone ($[\alpha]_D = -110°$, c=0.1 in $CHCl_3$).

EXAMPLE 17

In a manner analogous to that described in Example 15, using 100 mg of racemic ε-pyrromycinone, there were obtained 9 mg of cinerubin A (m.p. 130° C.) and 7 mg of cinerubin B (m.p. 150° C.), of the natural type respectively, as well as 44 mg of (7R, 9S, 10S)-ε-pyrromycinone.

EXAMPLE 18

In a manner analogous to that described in Example 15, using 100 mg of racemic 4-deoxy-ε-pyrromycinone, there were obtained 6 mg of 4-deoxy-cinerubin A and 6 mg of 4-deoxy-cinerubin B, of the natural type respectively, as well as 42 mg of (7R, 9S, 10S)-4-deoxy-ε-pyrromycinone.

EXAMPLE 19

In a manner analogous to that described in Example 15, using 100 mg of racemic auramycinone, there were obtained 8 mg of auramycin A (m.p. 141° C., $[\alpha]_D = -8.0°$, c=0.1 in $CHCl_3$) and 4 mg of auramycin B (m.p. 161° C., $[\alpha]_D = -8.0°$, c=0.1 in $CHCl_3$), of the natural type respectively, as well as 43.5 mg of (7R, 9S, 10S)-auramycinone.

EXAMPLE 20

In a manner analogous to that described in Example 15, using 100 mg of racemic 4-fluoro-aklavinone, there were obtained 9 mg of 4-fluoro-aclacinomycin A and 9 mg of 4-fluoro-aclacinomycin B, of the natural type respectively, as well as 35 mg of (7R, 9S, 10S)-4-fluoro-aklavinone.

EXAMPLE 20a

In a manner analogous to that described in Example 15, using 100 mg of racemic 4-deoxy-auramycinone, there were obtained 12 mg of 4-deoxy-auramycin A and 5 mg of 4-deoxy-auramycin B, of the natural type respectively, as well as 40 mg of (7R, 9S, 10S)-4-deoxy-auramycinone.

EXAMPLE 21

A solution of 0.921 g (2.63 mmol) of 2-ethyl-5-hydroxy-7-methoxy-3,4-dihydronaphthacene-1-(2H),6,11-trione, mp 224°–225°(dec), anhydrous methylene chloride was treated with 0.5 ml (3.945 mmol) of trimethylsilylcyanide at 25°. To this mixture was added 10 mg of anhydrous zinc iodide (catalyst). The reaction was allowed to proceed for one week and an additional 0.25 ml of trimethylsilylcyanide was added. After an additional 2 days at 25°, the mixture was partitioned between water/methylene chloride. The organic phase was dried and evaporated to afford 1β,2α-2-ethyl-1,2,3,4,6,11-hexahydro-5-hydroxy-7-methoxy-1-[(trimethylsilyl)oxy]-6,11-dioxonaphthacene-1-carbonitrile, mp 205°–206° (ethyl acetate) as an orange solid.

EXAMPLE 21a

Starting from 2-ethyl-5-hydroxy-3,4-dihydronaphthacene-1-(2H),b,11-trione by the same method described in Example 21, 1β,2α-2-ethyl-1,2,3,4,6,11-hexahydro-5-hydroxy-1-[(trimethylsilyl)oxy]-6,11-dioxonaphthacene-1-carbonitrile was obtained.

EXAMPLE 22

A solution of 400 mg (0.891 mmol) of 1β,2α-2-ethyl-1,2,3,4,6,11-hexahydro-5-hydroxy-7-methoxy-1-[(trimethylsilyl)oxy]-6,11-dioxonaphthacene-1-carbonitrile in 30 ml of methylene chloride/methanol, 1:1 was treated with 9.10 g (66.83 mmol) of potassium bisulfate at 25° under argon. After 15 min, the reaction was evaporated to dryness yielding 1β,2α-2-ethyl-1,2,3,4,6,11-hexahydro-1,5-dihydroxy-7-methoxy-6,11-dioxonaphthacene-1-carbonitrile intimately mixed with potassium bisulfate. This residue was heated in vacuo at 130° for 15 min, cooled, and triturated with methylene chloride to dissolve the product. Upon evaporation, the residue obtained was chromatographed over 300 g of silica, eluting with methylene chloride/methanol, 99:1. The product, 2-ethyl-3,4,6,11-tetrahydro-5-hydroxy-7-methoxy-6,11-dioxo-1-naphthacenecarbonitrile, was obtained at $R_f=0.6$, as 252 mg (82%) of an amorphous yellow-orange powder. This material was dissolved in 40 ml of anhydrous methylene chloride and treated with 1.0 g (7.49 mmol) of aluminum trichloride in one portion at 25°. The reaction was allowed to run for 16 h and then partitioned between N hydrochloric acid (ice)/methylene chloride. The organic phase was dried and evaporated to yield 2-ethyl-3,4,6,11-tetrahydro-5,7-dihydroxy-6,11-dioxo-1-naphthacenecarbonitrile, mp 277°–228° (ethyl acetate), as an orange solid.

EXAMPLE 22a

The same process described in Example 22, but starting from 1β,2α-2-ethyl-1,2,3,4,6,11-hexahydro-5-hydroxy-1-[(trimethylsilyl)oxy]-6,11-dioxonaphthacene-1-carbonitrile, gave 2-ethyl-3,4,6,11-tetrahydro-5-hydroxy-6,11-dioxo-1-naphthacenecarbonitrile.

EXAMPLE 23

A solution of 7.3 g (21.73 mmols) of 2-ethyl-5,7-dihydroxy-3,4-dihydronaphthacene-1-(2H),6,11-trione, mp 203°–204° in 265 ml of anhy methylene chloride was treated at 25° with 8.3 ml (65.19 mmols) of trimethylsilylcyanide and 1.32 g (4.13 mmols) of anhy zinc iodide catalyst. The mixture was stirred at room temperature for two days. The reaction was partitioned between water/methylene chloride. The aqueous phase was further extracted 4x with methylene chloride. The organic phases were combined, dried over sodium sulfate and evaporated to yield 1β,2α-2-ethyl-1,2,3,4,6,11-hexahydro-5,7-dihydroxy-1-[(trimethylsily)oxy]-6,11-dioxonaphthacene 1-carbonitrile as an orange solid.

EXAMPLE 24

A solution of 9.47 g (21.73 mmols) of 1β,2α-2-ethyl-1,2,3,4,6,11-hexahydro-5,7-dihydroxy-1-[(trimethylsilyl)oxy]-6,11-dioxonaphthacene-1-carbonitrile in 500 ml of methylene chloride/methanol, 1:1 was treated with 120 g of potassium bisulfate at 25° under argon. The reaction was allowed to proceed for 15 min at 25° and was filtered. The solid was washed 2x with methylene chloride/methanol, 1:1, and the filtrate was then evaporated to dryness to yield 1β,2α-2-ethyl-1,2,3,4,6,11-hexahydro-1,5,7-trihydroxy-6,11-dioxonaphthacene-1-carbonitrile as an orange solid.

EXAMPLE 25

An intimate mixture of 3.63 g (10.0 mmols) of 1β,2α-2-ethyl-1,2,3,4,6,11-hexahydro-1,5,7-trihydroxy-6,11,-dioxonaphthacene-1-carbonitrile and 40 g potassium bisulfate was heated at 135° in vacuo for 15 min. The mixture was cooled and placed in a filter funnel. The product was washed off the potassium bisulfate with methylene chloride/methanol, 9:1. The filtrate was evaporated and the residue chromatographed over silica, eluting with methylene chloride/acetone, 95:5. Fractions containing the product were combined and evaporated to afford 2-ethyl-3,4,6,11-tetrahydro-5,7-dihydroxy-6,11-dioxo-1-naphthacenecarbonitrile, mp 227°–228°.

EXAMPLE 26

An intimate mixture of 9.47 g (21.73 mmols) of 1β,2α-2-ethyl-1,2,3,4,6,11-hexahydro-5,7-dihydroxy-1-[(trimethylsilyl)oxy]-6,11-dioxonaphthacene-1-carbonitrile and 120 g potassium bisulfate was pyrolyzed at 135° in vacuo for 25 min. The mixture was cooled and placed in a filter funnel. The product mixture was eluted from the potassium bisulfate by a thorough washing with methylene chloride/methanol, 9:1. The filtrate was concentrated to afford 9.8 g of residue which was chromatographed over 0.5 kg silica, eluting with methylene chloride/acetone, 95:5. Fractions containing the desired product were combined and evaporated to afford 2-ethyl-3,4,6,11-tetrahydro-5,7-dihydroxy-6,11-dioxo-1-naphthacenecarbonitrile, mp 227°–228° (ethyl acetate) as an orange solid.

EXAMPLE 27

A solution of 10 mg (0.0229 mmol) of 1β,2α-2-ethyl-1,2,3,4,6,11-hexahydro-5,7-dihydroxy-1-[(trimethylsilyl)oxy]-6,11-dioxonaphthacene-1-carbonitrile in 5 ml anhy toluene was treated with 30 mg of p-toluenesulfonic acid hydrate and heated under reflux for 5 h. The reaction was cooled, washed with 10% bicarbonate, dried over sodium sulfate, and evaporated. The residue was chromatographed over silica, eluting with methylene chloride/acetone, 95:5. Fractions containing the desired product were combined and evaporated to yield 2-ethyl-3,4,6,11-tetrahydro-5,7-dihydroxy-6,11-dioxo-1-naphthacenecarbonitrile, mp 227°–228° (ethyl acetate).

EXAMPLE 28

To a suspension of 217 mg (0.629 mmol) of 2-ethyl-3,4,6,11-tetrahydro-5,7-dihydroxy-6,11-dioxo-1-naphthacenecarbonitrile in 25 ml of methanol was added 6 ml of 30% hydrogen peroxide and 3 ml of N sodium hydroxide. The solution was stirred at 25° for 3 h and partitioned between N hydrochloric acid/methylene chloride. The organic phase was dried and evaporated to yield 2α-ethyl-1α,2,3,5,10,11b-hexahydro-4,6-dihydroxy-5,10-dioxonaphthaceno [1,2-b]oxirene-11b-carboxamide, mp 263°–264° (THF/methanol/pet. ether) as a bright orange solid.

EXAMPLE 28a

Starting from 2-ethyl-3,4,6,11-tetrahydro-5-hydroxy-6,11-dioxo-1-naphthacenecarbonitrile, oxidation according to the procedure described in Example 28 gave 1α-ethyl-1α,2,3,5,10,11b-hexahydro-4-hydroxy-5,10-dioxonaphthaceno[1,2-b]oxirene-11b-carboxamide.

EXAMPLE 29

A solution of 200 mg (0.528 mmol) of 1α-ethyl-1α,2,3,5,10,11b-hexahydro-4,6-dihydroxy-5,10-dioxonaphthaceno [1,2-b] oxirene-11b-carboxamide in 85 ml of anhydrous methylene chloride was treated with 86 mg (0.581 mmol) of trimethyloxonium tetrafluoroborate at 25° under argon. After 5 h the reaction was partitioned between 10% of sodium bicarbonate/methylene chloride. The organic phase was dried and evaporated to afford 220 mg (96%) of the desired imidate ester intermediate. This material was immediately dissolved in 70 ml of THF and treated with 50 ml of 0.1 N sulfuric acid. The solution was heated at 45° for 2 days, cooled, and partitioned between water/methylene chloride. The organic layer was dried and evaporated. The residue was chromatographed over silica, eluting with methylene chloride/acetone, 88:12. The starting material (carboxamide) was recovered at $R_f=0.15$ and amounted to 90 mg. At $R_f=0.5$, the product, 1α-ethyl-1α,2,3,5,10,11b-hexahydro-4,6-dihydroxy-5,10-dioxonaphthaceno[1,2-b]oxirene-11b-carboxylic acid, methyl ester, was obtained as an orange solid, mp 229°–230° (ethyl acetate, pet. ether).

EXAMPLE 29a

Starting from 1α-ethyl-1α,2,3,5,10,11b-hexahydro-4-hydroxy-5,10-dioxonaphthaceno [1,2-b]oxirene-11b-carboxamide, by the procedure described in Example 29, 1α-ethyl-1α,2,3,5,10,11b-hexahydro-4-hydroxy-5,10-dioxonaphthaceno[1,2-b]oxirene-11b-carboxylic acid methyl ester was obtained.

EXAMPLE 30

A solution of 4.0 mg of 1α-ethyl-1α,2,3,5,10,11b-hexahydro-4,6-dihydroxy-5,10-dioxonaphthaceno[1,2-b]oxirene-11b-carboxylic acid, methyl ester in 3.5 ml of acetic acid/water, 3:1 was treated with 10 mg of zinc dust at 25°. After one hour, the reaction was partitioned between water/methylene chloride. The organic phase was dried and evaporated. The residue was chromatographed over silica eluting with methylene chloride/acetone, 95:5. The product, racemic 2β-ethyl-1,2,3,4,6,11-hexahydro-2α,5,7-trihydroxy-6,11-dioxo-1β-naphthacenecarboxylic acid, methyl ester, was isolated at $R_f=0.3$ as an orange solid, mp 210°-211° (ethyl acetate/pentane). The product is also known as racemic 7-deoxyaklavinone.

EXAMPLE 30a

The reduction described in Experiment 30 but starting from 1α-ethyl-1α,2,3,5,10,11b-hexahydro-4-hydroxy-5,10-dioxonaphthaceno[1,2-b]oxirene-11b-carboxylic acid methyl ester led to racemic 2β-ethyl-1,2,3,4,6,11-hexahydro-2α,5-dihydroxy-6,11-dioxo-1β-naphthacenecarboxylic acid methyl ester.

EXAMPLE 31

A sample of 15.0 mg (0.0379 mmol) of 2β-ethyl-1,2,3,4,6,11-hexahydro-2α,5,7-trihydroxy-6,11-dioxo-1-naphthacenecarboxylic acid methyl ester (7-deoxyaklavinone) was dissolved in 15 ml of hot carbon tetrachloride and cooled to room temperature. To this solution was added 30 μl distilled water, 7.0 mg (0.0393 mmol) of N-bromosuccinimide, and 1.5 mg of 2,2'-azobis-(2-methylpropionitrile), catalyst. The mixture was heated under reflux for 0.5 h. At this point, an additional 2.0 mg (0.0112 mmol) of N-bromosuccinimide was added and the reaction was allowed to proceed under reflux of 0.5 h more. The mixture was cooled to 25° and treated with 15 ml of tetrahydrofuran and 7.5 ml 10% potassium carbonate. After stirring for 10 minutes at 25° C., the reaction was partitioned between 1 N hydrochloric acid and methylene chloride. The aqueous phase was further extracted 3x with methylene chloride. The organic phases were dried over sodium sulphate and evaporated to afford 16.0 mg of crude product. This material was chromatographed on thick layer silica plates, eluting with methylene chloride 93/acetone 7. This purification afforded pure 2β-ethyl-1,2,3,4,6,11-hexahydro-2α,4α,5,7-tetrahydroxy-6,11-dioxo-1-naphthacenecarboxylic acid methyl ester (also known as aklavinone), m.p. 170°-171.5° C. (abs. ethanol).

EXAMPLE 31a

Hydroxylation described in Example 30, but starting from racemic 2β-ethyl-1,2,3,4,6,11-hexahydro-2α,5-dihydroxy-6,11-dioxo-1-naphthacenecarboxylic acid methyl ester gave racemic 4-deoxy-aklavinone.

EXAMPLE 32

In a similar fashion 4.0 mg (0.0101 mm) of racemic 2β-ethyl-1,2,3,4,6,11-hexahydro-2α,5,7-trihydroxy-6,11-dioxo-1-naphthacenecarboxylic acid methyl ester (racemic 7-deoxyaklavinone) was converted to racemic 2β-ethyl-1,2,3,4,6,11-hexahydro-2α,4α,5,7-tetrahydroxy-6,11-dioxo-1-naphthacenecarboxylic acid methyl ester (also known as racemic aklavinone), mp 205°-206° (abs. ethanol).

EXAMPLE 33

A solution of 360 mg (0.914 mmol) of 1α-ethyl-1α,2,3,5,10,11b-hexahydro-4,6-dihydroxy-5.10-dioxonaphthaceno[1,2-b]oxirene-11b-carboxylic acid, methyl ester in 50 ml abs ethanol was treated with 35 ml triethanol amine and hydrogenated for 1.5 h at 25° (one atmosphere) using 140 mg of 10% Pd/Ba SO₄ catalyst. The mixture was partitioned between N sulfuric acid/methylene chloride. The organic phase was dried over sodium sulfate and evaporated. The residue was chromatographed over 300 g silica, eluting with methylene chloride/acetone, 95:5. Fractions containing the product were combined and evaporated to afford pure 2β-ethyl-1,2,3,4,6,11-hexahydro-2, 5,7-trihydroxy-6,11-dioxo-1β-naphthacenecarboxylic acid, methyl ester, mp 210°-211° (ethyl acetate/pentane). This product is also known as (±)-7-deoxyaklavinone and (±)-galirubinone.

EXAMPLE 34

To 40 ml of carbon tetrachloride was added 38.2 mg (0.1 mmol) of 2β-methyl-1,2,3,4,6,11-hexahydro-2α,5,7-trihydroxy-6,11-dioxo-1-naphthacenecarboxylic acid methyl ester (7-deoxyauramycionone), and the mixture was heated to effect solution. After cooling to 25° C., the solution was treated with 20 mg (0.112 mmol) of N-bromosuccinimide, 80 μl distilled water and 5 mg of 2,2'-azobis-(2-methylpropionitrile), catalyst. This mixture was heated under reflux for 0.5 h and an additional 5 mg (0.0281 mmol) of N-bromosuccinimide was added. After a further 0.25 h of reflux period, the reaction was cooled to room temperature and treated with 50 ml of tetrahydrofuran and 25 ml of 10% potassium carbonate. The mixture was stirred for 10 minutes and then partitioned between 1 N hydrochloride acid/methylene chloride. The aqueous phase was further extracted 3x with methylene chloride. The organic extracts were dried over sodium sulfate and evaporated to yield 65 mg of residue. The product was further purified by thick layer chromatography over silica, eluting with methylene chloride 93/acetone 7, yielding pure 2β-methyl-1,2,3,4,6,11-hexahydro-2α,4 α,5,7-tetrahydroxy-6,11-dioxo-1-naphthacenecarboxylic acid methyl ester (auramycinone) mp 163°-165° C. (abs. ethanol).

EXAMPLE 35

A solution of 41.2 mg (0.1 mmol) of 2β-ethyl-1,2,3,4,6,11-hexahydro-2α,5,7,10-tetrahydroxy-6,11-dioxo-1-naphthacenecarboxylic acid methyl ester (7-deoxy-ε-pyrromycinone) in 40 ml of carbon tetrachloride was treated with 80 ul of distilled water, 20 mg (0.112 mmol) of N-bromosuccinimide, and 5 mg of 2,2'-azobis-(2-methylpropionitrile). The mixture was heated under reflux for 0.5 h, cooled, and hydrolyzed with 50 ml of tetrahydrofuran/25 ml of 10% potassium carbonate for 10 min. The reaction was acidified with N H₂SO₄ and extracted 3x with methylene chloride. The organic phases were dried over sodium sulfate and evaporated to afford 68 mg of residue. The product was purified by thick layer chromatography over silica, eluting with toluene/CH$_3$OH, 25:1 to afford pure 2β-methyl-1,2,3,4,6,11-hexahydro-2α,4α,5,7,10-pentahydroxy-6,11-dioxo-1-naphthacenecarboxylic acid methyl ester (ϵ-pyrromycinone) mp 237°–238° C. (EtOAc).

EXAMPLE 36

A solution of 42.4 mg (0.1 mmol) of 2β-(2-oxopropyl)-1,2,3,4,5,11-hexahydro-2 α,5,7-trihydroxy-6,11-dioxo-1-naphthacenecarboxylic acid methyl ester (7-deoxysulfurmycinone) in 40 ml of carbon tetrachloride was treated with 80 μl of distilled water, 20 mg (0.112 mmol) of N-bromosuccinimide, and 5 mg of 2,2'-azobis-(2-methylpropionitrile). The mixture was heated under reflux for 0.5 h and then treated with an additional 5 mg of NBS. After 15 min, the reaction was cooled, 50 ml of tetrahydrofuran/25 ml of 10% potassium carbonate was added, and the mixture was stirred for 10 min at 25°. The product was partitioned between N sulfuric acid/methylene chloride, and the organic phases were dried over sodium sulfate and evaporated to afford 75 mg of residue. The product was isolated by thick layer chromatography over silica, eluting 2x with toluene/CH$_3$OH, 25:1, to afford 2β-(2-oxopropyl)-1,2,3,4,6,11-hexahydro-2α,4α,5,7-tetrahydroxy-6,11-dioxo-1-naphthacenecarboxylic acid methyl ester (sulfurmycinone), mp 159°–160° C. (EtOAc/Pet. Ether).

EXAMPLE 37

The starting material of formula II wherein R$_1$ is hydrogen is produced by fermentation utilizing strains of Streptomyces galilaeus which are on deposit at the American Type Culture Collection, Rockville, Md. The strains which may be utilized have the following designations and accession numbers:

|  | ATCC No. |
| --- | --- |
| Streptomyces galilaeus OBB-111 | 31533 |
| Streptomyces galilaeus FR-401 | 31535 |
| Streptomyces galilaeus OBB-111-610 | 31534 |

Following the below procedure but utilizing other of the above strains of Streptomyces galilaeus one can produce the starting material of formula II wherein R$_1$ is hydrogen.

The scraped spores from an agar slant of Streptomyces galilaeus OBB-111 (FERM-P No. 4780) were transferred to a 500 ml Erlenmeyer flask containing 100 ml of sterilized medium consisting of 20.0 g D-glucose, 20.0 g soluble starch, 5.0 g S-3 meat (Ajinomoto Co., Ltd.), 2.5 g yeast extract (Daigo Eiyo-Kagaku Co., Ltd.), 1.0 g K$_2$HPO$_4$, 1.0 g MgSO$_4$.7H$_2$O, 3.0 g NaCl and 3.0 g CaCO$_3$ made up to one liter with tap water. This vegetative culture was incubated at 27° C. on a rotary shaker set at 180 rpm. After 72 hours, two ml of culture were transferred to a 500 ml Erlenmeyer flask containing 100 ml of sterile production medium consisting of 20.0 g D-glucose, 20.0 g soluble starch, 10.0 g Pharmamedia (Traders Oil Mill Co., U.S.A.), 1.0 g K$_2$HPO$_4$, 1.0 g MgSO$_4$.7H$_2$O, 3.0 g NaCl and 3.0 g CaCO$_3$ made up to one liter with tap water. The culture was incubated at 27° C. for 72–96 hours on a rotary shaker set at 180 rpm.

At this time, antibiotic activity of the culture filtrate and the mycelial extract, measured by paper disc agar diffusion method, using Sarcina lutea IMA-1009 as a test microorganism, was 22 mm and 30 mm in diameter respectively.

(a) 600 ml of the vegetative culture obtained in a manner analogous to that as described above were transferred to a 50 liter jar containing 30 liters of sterile production medium containing the same components as described above and including 0.1% Nissan Disfoam (Nippon Yushi Co., Ltd.). The cultivation was carried out at 27° C. with the agitation of 350 rpm and aeration 1 v/v medium. After approximately 90 hours, the incubation was terminated.

(b) Then the culture was centrifuged. The filtrate and the cake thus obtained were extracted separately. The cake was suspended in 15 liters of methanol, stirred for 3 hours and filtered, and the cake was further extracted with methanol once again. To the extract thus obtained, 30 liters of chloroform and 30 liters of water were added and mixed, and the chloroform layer was obtained. On the other hand, the culture filtrate was extracted with 60 liters of a solvent mixture of chloroform and methanol (1:1), and the chloroform layer was obtained. The chloroform extracts from the cell cake and the culture filtrate were combined and evaporated to a small volume (50–60 ml). The concentrate was diluted with n-hexane to precipitate a yellow solid and dried in vacuo to give 4.8 g of a mixture of auramycin A, auramycin B, sulfurmycin A, sulfurmycin B, auramycinone, sulfurmycinone, 7-deoxyauramycinone and 7-deoxysulfurmycinone.

(c) Fractionation of said mixture was carried out. Sephadex LH-20 soaked for 15 hours in a solvent mixture of chloroform and methanol (2:1, v/v) was packed into a column of 50 cm in length and 5.0 cm in diameter. The mixture obtained above (4.8 g) was dissolved in 10 ml of a mixture of chloroform and methanol (2:1, v/v) and applied to the column. The column was eluted with a mixture of chloroform:methanol (2:1, v/v). As a result two distinct bands of anthracyclines were noted. One was shown by thin layer chromatography on silica gel (chloroform:methanol, 19:1, v/v) to be a mixture mainly of 7-deoxyauramycinone (formula II compound) and 7-deoxysulfurmycinone (formula II compound) and small amounts of auramycinone and sulfurmycinone. The fractions containing said mixture were concentrated to dryness in vacuo and 1.2 g of yellow solid were obtained.

(d) 1.2 g of the yellow solid consisting mainly of 7-deoxyauramycinone and 7-deoxysulfurmycinone and of minor amounts of auramycinone and sulfurmycinone obtained in step (c) were mixed with silica gel and subjected to column chromatography on silica gel (column 25×2.5 cm) using a mixture of chloroform and n-hexane (4:1, v/v) as eluent. First 7-deoxyfulfurmycinone (formula II compound) was eluted followed by 7-deoxyauramycinone (formula II compound) sulfurmycinone and auramycinone in this order. The fractions containing only one compound were concentrated to dryness in vacuo. Pure 7-deoxysulfurmycinone and 7-deoxyauramycinone, (compounds of formula II) respectively were obtained as yellow powder.

What is claimed is:

1. A process for producing optically active anthracycline glycosides A and B with 7S-configuration comprising stereoselectively glycosidating an enantiomer with 7S-configuration starting from a racemic anthracyclinone by means of Streptomyces galilaeus OBB-111-848 (FERM-P No. 5316, ATCC 31598).

2. A process according to claim 1 wherein the stereoselective glycosidation is carried out by adding a racemic anthracyclinone as a substrate to *Streptomyces galilaeus* OBB-111-848 (FERM-P No. 5316, ATCC 31598) fermenting in a culture medium and recovering an optically active anthracycline glycosides A and B with 7S-configuration, respectively from the fermentation broth.

3. A process according to claim 1 wherein the stereoselective glycosidation is carried out in the presence of mycelium isolated from the culture broth of *Streptomyces galilaeus* OBB-111-848 (FERM-P No. 5316, ATCC 31598), in a solution.

4. A process according to claim 2 or claim 3 wherein the substrate is a racemic alkavinone, 4-deoxy-aklavinone, ε-pyrromycine, 4-deoxy-ε-pyrromycine, auramycine, 4-deoxy-auramycine or 4-fluoro-aklavinone.

5. A process according to claim 2 or claim 3 wherein the substrate concentration amounts to 50–800 mg/l.

6. A process according to claim 2 or claim 3 wherein a solution of the substrate in an organic solvent is used in the stereoselective glycosidation.

* * * * *